United States Patent [19]

Chauvette et al.

[11] Patent Number: 5,718,697
[45] Date of Patent: Feb. 17, 1998

[54] LIQUID ABSORBENT SPHAGNUM MOSS ARTICLE AND METHOD FOR MANUFACTURING THE ABSORBENT ARTICLE

[75] Inventors: Gaetan Chauvette, St-Hubert; Martin Roy, Lachenair, both of Canada

[73] Assignee: Johnson & Johnson, Inc., Montreal, Canada

[21] Appl. No.: 572,376

[22] Filed: Dec. 14, 1995

[51] Int. Cl.$^6$ .............................. A61F 13/15; A61F 13/20
[52] U.S. Cl. .......................... 604/367; 428/191; 428/225; 604/374
[58] Field of Search ...................... 604/358, 364, 604/367, 374, 375, 385.1; 428/191, 225

[56] References Cited

U.S. PATENT DOCUMENTS

| | | | |
|---|---|---|---|
| 5,180,622 | 1/1993 | Berg et al. | 604/368 |
| 5,374,260 | 12/1994 | Lemay et al. | 604/380 |
| 5,569,239 | 10/1996 | Emenaker et al. | 604/358 |

*Primary Examiner*—P. Zuttarelli
*Attorney, Agent, or Firm*—James P. Barr

[57] ABSTRACT

A liquid-absorbent article having a high absorption capacity and a short fluid penetration time. The liquid-absorbent article comprises sphagnum moss material containing an effective amount of cross-linked cellulosic fibers. The liquid-absorbent article is well-suited for use as an absorbent component of a disposable absorbent product, such as a sanitary napkin, a diaper, an incontinence pad, an adult brief, a wound dressing, a nursing pad, a tampon pledger, or as desiccant for packaging materials to keep goods dry during shipping or storage. The invention also extends to a novel method for manufacturing the liquid-absorbent article.

15 Claims, 3 Drawing Sheets

LIQUID ABSORBENT SPHAGNUM MOSS ARTICLE AND METHOD FOR MANUFACTURING THE ABSORBENT ARTICLE

FIELD OF THE INVENTION

The invention relates to the art of manufacturing structures for absorbing body exudate. More specifically, the invention relates to a highly absorbent article that is capable of fast liquid acquisition and possesses a high absorbent capacity. The absorbent article includes sphagnum moss material incorporating an effective amount of cross-linked fibers. The invention also extends to a method for manufacturing the sphagnum moss absorbent article.

BACKGROUND OF THE INVENTION

Many disposable absorbent products use absorbent cores made primarily of cellulosic pulp fluff material. Such cores are generally soft, flexible and absorbent but tend to be bulky and thick and have poor wicking properties. In addition, cellulosic pulp fluff material has poor structural stability which may cause the absorbent core to collapse when saturated with liquid.

An absorbent structure that has poor wicking properties usually increases the likelihood of failure of the absorbent product to hold and contain body liquids. Body exudate will be localised to a certain area of the poorly wicking absorbent medium, causing localized saturation whereby excess liquid may overflow through an external surface of the absorbent product. This overflow may contact the user's garment and cause stains or contact the user's body and cause wet discomfort or rash. It is therefore desirable to provide an absorbent core for disposable absorbent products which can wick away body liquids from the point of contact with the absorbent core and spread it through the absorbent core. The improved wicking properties of such an absorbent core provide the capacity for liquids to travel by capillary pressure throughout the entire absorbent volume. This permits the use of thinner cores, since more absorbent volume can be made available for absorbing body liquids by such wicking action. Thinner absorbent cores may also prove to be more comfortable for the user and less unsightly or obvious when worn under clothes.

Absorbent cores with excellent wicking properties comprising sphagnum moss are described, for example, in the following US patents:

| PATENT # | INVENTOR (s) | DATE OF ISSUE |
| --- | --- | --- |
| 4,170,515 | Lalancette et al. | October 9, 1979 |
| 4,215,692 | Levesque | August 5, 1980 |
| 4,226,237 | Levesque | October 7, 1980 |
| 4,305,393 | Nguyen | December 15, 1981 |
| 4,473,440 | Ovans | September 25, 1984 |
| 4,507,122 | Levesque | March 26, 1985 |
| 4,618,496 | Brasseur | October 21, 1986 |
| 4,676,871 | Cadieux et al. | June 30, 1987 |
| 4,992,324 | Dubé | February 12, 1991 |
| 5,053,029 | Yang | October 1, 1991 |

The subject matter of these patents is incorporated herein by reference.

In accordance with the teaching of these patents, an absorbent structure comprising sphagnum moss as a primary absorbent component is formed as a sheet by air or wet laying of particles. The sheet is calendered to obtain a relatively thin, i.e. from about 0.025 to about 0.25 centimeters (cm) thick and relatively dense, i.e. from about 0.1 to about 1.0 grams per cubic centimeter (g/cc) structure. Such absorbent sphagnum moss sheet may be processed to increase its flexibility for enhancing its comfort potential by subjecting the sheet to mechanical tenderizing such as a perf-embossing or a micro-corrugating process.

The sphagnum moss sheet thus formed has a large proportion of extremely tiny interstices allowing the sheet to absorb and retain a very high amount of liquid. The sphagnum moss interstices swell as they absorb liquid, however, this swelling does not cause a loss of capacity for further admitting liquid. Rather, the swelling contributes to the ability of the absorbent medium to retain the liquid while generally maintaining the structural integrity of the absorbent structure in use.

The wicking properties of the above-described sphagnum moss sheet provide the ability for the sheet to be highly absorbent while remaining relatively thin.

Although sphagnum moss has certain highly desirable liquid-absorption properties, it manifests less than ideal fluid-acquisition rates. To overcome this difficulty it is common practice to provide a highly permeable, fibrous, liquid transfer layer on the sphagnum moss layer, whose function is to quickly collect the body exudate and then meter the liquid to the sphagnum moss material. Liquid discharged on such composite absorbent structure will rapidly ingress the transfer layer due to its highly porous network. From the transfer layer, liquid migrates toward the sphagnum moss layer by capillary pressure as a result of the substantial difference in wicking power between the different materials. The liquid migration is well-controlled, occurring at the rate of acceptance of the sphagnum moss.

Compound absorbent structures including transfer and reservoir layers are costly to produce because the raw material for manufacturing the transfer layer is expensive. Another drawback is the undesirable bulk increase of the disposable absorbent article resulting from the use of a thick transfer layer.

Hence, there is a need in the industry to provide a sphagnum moss absorbent core having a significantly improved liquid acquisition rate, thus allowing to employ a thinner transfer layer and possibly eliminate the transfer layer altogether.

OBJECTIVES AND STATEMENT OF THE INVENTION

The prime objective of the invention is to provide an absorbent article that has a high liquid-acquisition rate, the ability to wick away liquid from the point of impact and a high absorption capacity.

Another object of the invention is to provide a disposable absorbent product, such as a sanitary napkin, a diaper, an incontinence pad, an adult brief, a wound dressing, a nursing pad, a tampon pledger, or a desiccant for packaging materials, which utilizes the aforementioned liquid-absorbent article as an absorbent component.

Another object of the invention is a method for manufacturing the aforementioned liquid-absorbent article.

As embodied and broadly described herein, the invention provides a liquid-absorbent article having a high fluid acceptance rate for use in a disposable liquid-absorbent product, said liquid-absorbent article comprising sphagnum moss material and an effective amount of cross-linked fibers. For the purpose of this specification the expression "effective amount of cross-linked fibers" means an amount sufficient to increase the average inter-particle interstice size of the sphagnum moss material for, in turn, increasing its rate of liquid absorption.

Sphagnum moss is a material characterized by a cellular organization that provides two different types of interstices capable of admitting and storing liquid, namely inter-particle interstices and intra-particle interstices. The intra-particle interstices are formed by the internal lumen of the sphagnum moss particles and they are very small. Consequently, the intra-particle interstices manifest a very strong capillary attraction and greatly contribute to the ability of the sphagnum moss material to wick away body liquids from the point of impact and distribute the liquid throughout the entire absorbent material. The inter-particle interstices, on the other hand, are formed between the sphagnum moss particles and they are considerably larger.

The cross-linked fibers provide a high-bulk, resilient structure capable of spacing apart the sphagnum moss particles. The resulting structure has a larger average inter-particle interstice size and it is capable of faster liquid acquisition by comparison to a sphagnum moss structure without cross-linked fibers. Interestingly, the cross-linked fibers do not significantly affect the average intra-particle interstice size. As a result, the absorbent structure according to the invention combines two attributes that are often considered incompatible, namely the ability to take-up liquid faster (resulting from larger inter-particle interstices) and the ability to wick away the liquid and distribute it through the entire absorbent volume (resulting from the small intra-particle interstices).

In a preferred embodiment, cross-linked cellulosic fibers are incorporated to the sphagnum moss material in the range from about 5% to about 75% based on the dry weight of the liquid absorbent article, more preferably, in the range from about 15% to about 40% and most preferably in the range from about 15% to about 30%.

Cross-linked cellulosic fibers and their method of manufacture are generally known to those skilled in the art. For example, the U.S. Pat. No. 4,853,086 granted to Weyerhaeuser company on Aug. 1, 1989 describes a method for manufacturing cross-linked cellulosic fibers which consists of spraying a wet or partially dry web of cellulosic fibers with an aqueous solution of glycol and dialdehyde. The disclosure of this patent is incorporated herein by reference.

As embodied and broadly described herein, the invention further provides a method for manufacturing a liquid-absorbent article having a high liquid acceptance rate and a high absorbent capacity, comprising the step of incorporating in a sheet of sphagnum moss material an effective amount of cross-linked fibers.

In a preferred embodiment cross-linked cellulosic fibers are added to a slurry of sphagnum moss material. The slurry is then formed into a web and dewatered to obtain the liquid-absorbent article in sheet form.

As embodied and broadly described herein, the invention also extends to a disposable, laminated liquid-absorbent product, comprising:

a) a liquid permeable cover layer;

b) a liquid impervious backing layer; and c) an absorbent component between said layers, said absorbent component comprising a sheet containing sphagnum moss material and an effective amount of cross-linked fibers.

The absorbent component may be a unitary structure or a laminated structure of the type comprising a top transfer layer and a bottom reservoir layer. The liquid absorbent article according to the invention possesses attributes making it suitable to use as a transfer layer or as a reservoir layer.

The fluid absorbent article according to the invention is suitable for use primarily in disposable absorbent products such as sanitary napkins, diapers, urinary pads, adult briefs, wound dressing, nursing pads, tampon pledgets, or as desiccants for packaging materials to keep goods dry during shipping or storage.

DETAILED DESCRIPTION OF A PREFERRED EMBODIMENT

Figure 1:
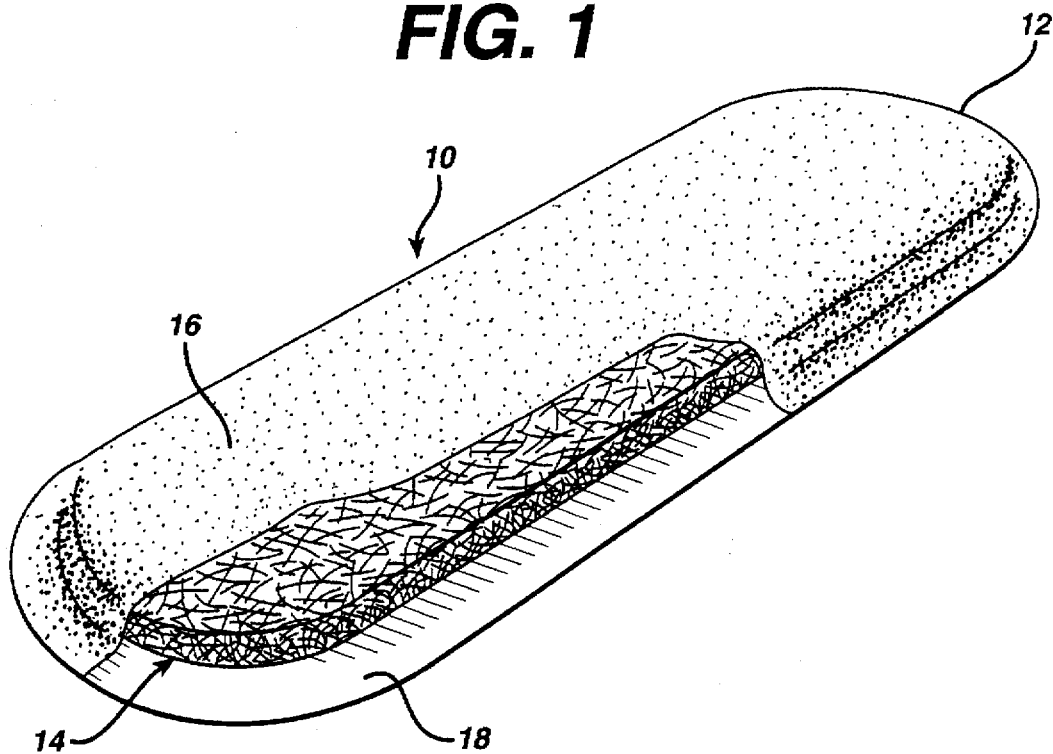
FIG. 1 is a fragmentary, perspective view of a sanitary napkin incorporating the liquid-absorbent article according to the invention.

Referring now to FIG. 1 of the annexed drawings, the reference numeral 10 designates comprehensively a sanitary napkin constructed in accordance with the principles of the present invention. The sanitary napkin 10 comprises an envelope 12 defining an internal space receiving an absorbent component 14 that includes sphagnum moss. The envelope 12 includes a liquid permeable cover layer 16 made of a non-woven fabric or any other suitable porous web or apertured film, and a liquid impervious backing layer 18, made of polyethylene film for example. The cover and backing layers 16 and 18 are heat-sealed to one another along their marginal portions. To attach the sanitary napkin 10 to the wearer's underpants, the liquid impervious backing layer 18 may be provided with adhesive zones covered with a peelable backing (not shown in the drawings).

The absorbent component 14 is a single layer structure. Preferably, a transfer layer (not shown in the drawings) of known construction is provided over the absorbent component with a view of enhancing the liquid acquisition rate of the sanitary napkin.

Figure 2:
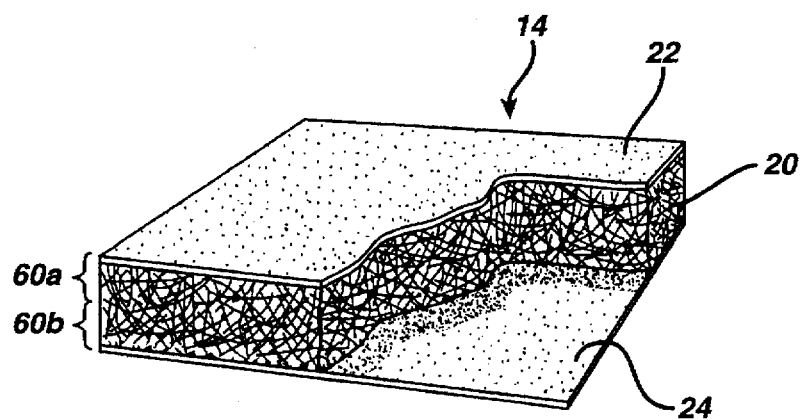
FIG. 2 is a fragmentary enlarged perspective view of the liquid-absorbent article according to the invention.

The structure of the absorbent component 14 is shown in FIG. 2. It comprises a central core 20 containing sphagnum moss intermixed with cross-linked cellulosic fibers that open-up the sphagnum moss material to provide a structure with an increased void volume capable of high liquid acceptance rate. In addition, the cellulosic fibers which are dispersed throughout the entire sphagnum moss material provide a "lead-in" action inducing fluid to enter the sphagnum moss material by virtue of their hydrophilicity. Hence, the central core 20 is capable of fast liquid acquisition. At the same time the central core 20 has the ability to efficiently wick away liquid from the point of impact due to the presence of intraparticle interstices that are very fine and manifest an intense capillary attraction.

The central core 20 is confined between reinforcing layers 22 and 24 of fibrous material. The purpose of the reinforcing layers is twofold. First, they strengthen the core 20, thereby providing a unitized absorbent structure capable of maintaining its integrity even when saturated with liquid. Second, the layers 22 and 24 reduce dusting by preventing free sphagnum moss particles within the absorbent structure from being released outside. Kraft wood pulp material has been found highly satisfactory for manufacturing the reinforcing layers 22 and 24. It is also possible to use other materials, such as cotton linters or ground wood among others, in admixture with or in substitution to the Kraft wood pulp material.

Figure 3:
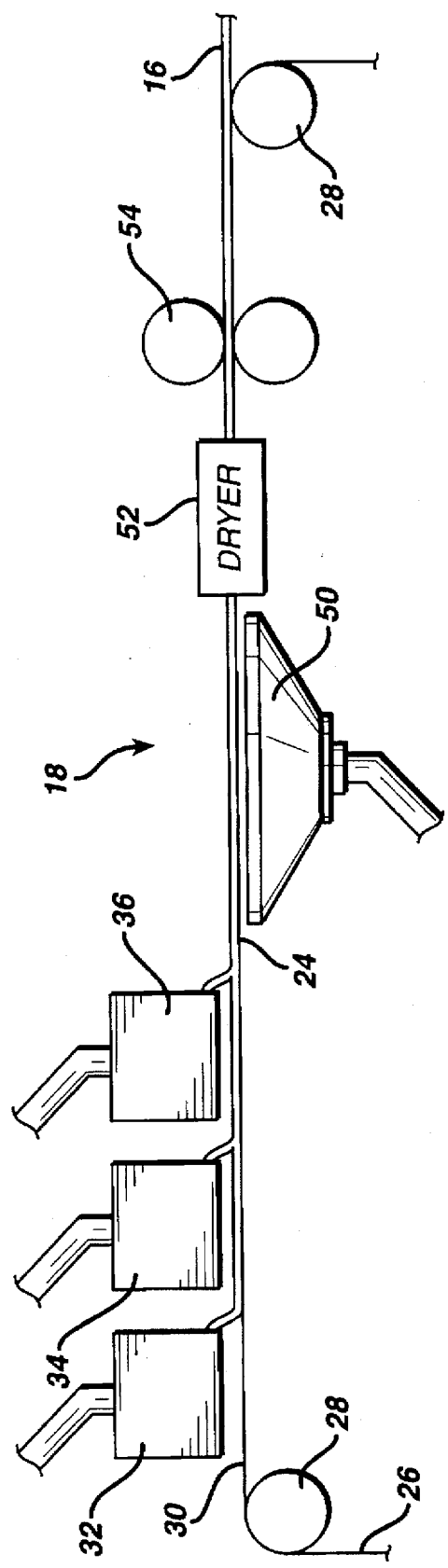
FIG. 3 is a schematic representation of an apparatus for manufacturing the liquid-absorbent article.

The detailed composition of the liquid-absorbent component 56 will be best understood from the following description of the apparatus and the process for manufacturing such absorbent component. Referring to FIG. 3, the apparatus designated comprehensively by the reference numeral 18, comprises an endless, fluid-pervious Fourdrinier wire 26 which is mounted on rollers 28 to provide a horizontally extending run 30 that is continuously advanced forward to support and convey a slurry of sphagnum moss and cellulosic fibers through various processing stations.

Headboxes 32, 34, and 36 arranged in a spaced apart relationship along the path of travel of the wire 26 are provided to lay on the wire 26 slurry in sheeted form. The headbox bank deposits on the wire 26 three (3) layers of slurry in a superposed relationship to form a laminated slurry web. More specifically, the headbox 34 lays a slurry containing sphagnum and cross-linked cellulosic fibers while the headboxes 32 and 36 deliver slurry of fibrous material such as Kraft wood pulp or any other suitable substance.

Figure 4:
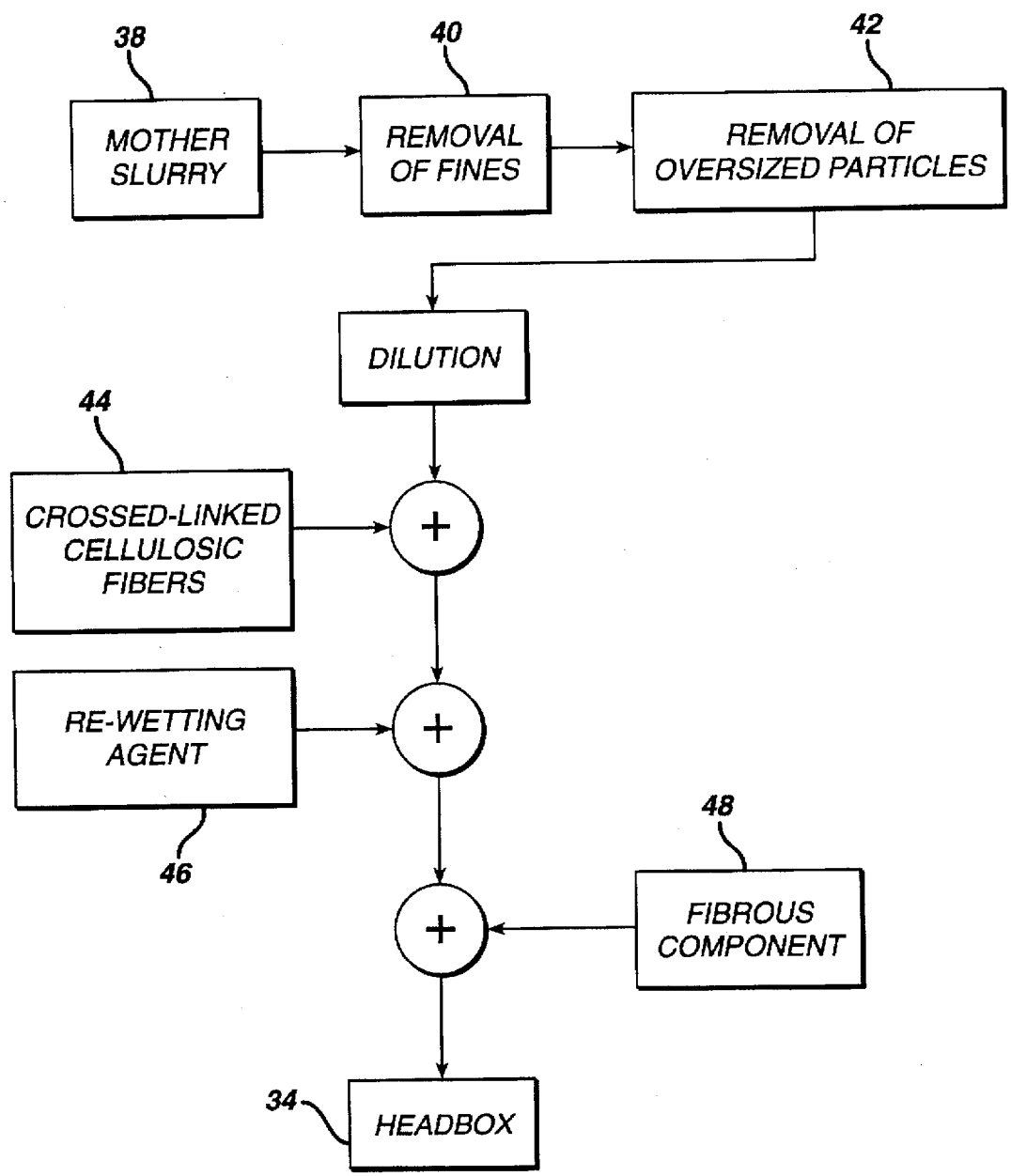
FIG. 4 is a flowchart of the process for manufacturing the liquid-absorbent article.

The sphagnum moss slurry supplied to the headbox 34 is prepared by the process depicted in FIG. 4. The starting sphagnum moss harvested from the bog should have a relatively high absorbent capacity. Sphagnum moss capable of absorbing and retaining at least about 25 and preferably about 50 times its weight in water has been satisfactory. The raw sphagnum moss is dispersed in water to create at step 38 a mother slurry which is then wet classified to remove the extremely fine material, commonly referred to as fines, and large pieces of material including roots, branches and the like that do not contribute significantly to the absorbency of the sphagnum moss material.

Generally speaking, the classification is carried out in two steps. Fines are removed at the first screening step 40, such that anything that passes through a number 60 mesh screen is discarded. At coarse screening step 42, anything that remains on a vibrating screen in the form of a perforated plate having apertures of 2 millimeters (mm) in diameter is discarded. Wet screening is the technique of choice for both screening steps 40 and 42. This dual-stage classification has the effect of retaining only the particles having a size in the range from about 74 microns to about 2000 microns. The screened fraction at the output of the coarse screening step 42 is diluted with water to render the slurry more manageable. Next, at step 44 cross-linked cellulosic fibers are added to the slurry in the range from about 5% to about 75% by weight of solids in the absorbent component 14, preferably from about 15% to about 40% and most preferably from about 15% to about 30%. Cross-linked fibers available from the Weyerhaeuser Paper Company, USA under the brand name NHB-405 or HBA-S have been found satisfactory.

Optionally a first re-wetting agent may be added to the slurry sphagnum moss/cross-linked cellulosic fibers, at step 46. Preferably, the amount of re-wetting agent is of 0.3% by weight of solids in the absorbent component 14. A re-wetting agent available from Clough Chemicals under the brand designation RL Thorowet has been found satisfactory.

If desired, a fibrous component may be added to the slurry, prior to delivering the slurry to the headbox 34, as shown at step 48. The fibrous component may include such materials as Kraft Wood pulp and mechanical wood pulp. As used herein, the term mechanical wood pulp is meant to include ground wood pulp, thermo-mechanical pulp and refiner wood pulp. Ground wood pulp is essentially trees and branches which have been debarked, cleaned and ground into particulate matter. Refiner wood pulp differs from ground wood pulp only in that the grind step utilizes a refiner, i.e. a disc-like device well-known in the art and having metallic ribs at the peripheral sections thereof which last contact the wood particles and help separate the wood fibers without excessively damaging them. Thermo-mechanical wood pulp is similar to refiner pulp with the exception that the wood particles are heated in the refiner, usually with steam, to add in separating the wood fibers. The common characteristic of these mechanical pulps is that no attempt has been made to separate the fibers by chemical means although they may later, after being reduced to fine particulate matter, be subjected to a desired chemical treatment, such as bleaching. Preferably, when mechanical wood pulp is used in a sphagnum moss slurry, such mechanical pulp has a Canadian Standard Freeness (TAPPI test method T-227), from about 60 to 750 and preferably from about 400 to 600.

The Kraft wood pulp, also usable in combination with sphagnum moss, is essentially chemically treated, long fibred wood pulp such as sulphite and sulphate wood pulps.

The fibrous component may also include a natural or synthetic textile fiber such as rayon, polyester, nylon, acrylic or the like, having a length of from about 0.6 cm to about 1.9 cm, preferably about 1.3 cm and a denier of from about 1.0 to 5.0, present in an amount from 2 to 20% by weight of the absorbent sheet 10, preferably from 2% to 6%.

After the addition of the fibrous component, the slurry is conveyed to the headbox 34 to be delivered on the Fourdrinier wire 26.

In a first example, a slurry of Kraft wood pulp having the consistency of about 0.2% by weight of solids is first laid down on the wire 26 from the headbox 32 in order to form the bottom Kraft reinforcing layer 24. The slurry flow rate is selected to deliver on the wire 26, 15 grams of solids per square meter. The Kraft slurry passes under the headbox 34 which delivers on top of the Kraft layer a slurry of sphagnum moss particles prepared by the process depicted in FIG. 4. The slurry has the following composition.

| CONSTITUENT | PROPORTION BY WEIGHT OF SOLIDS IN THE LIQUID ABSORBENT COMPONENT 14 |
| --- | --- |
| sphagnum moss | 62.7% |
| polyester fibers | 3.7% |
| Kraft wood pulp fibers | 7.9% |
| Cross-linked cellulosic fibers | 19.4% |

A final Kraft wood pulp slurry layer is laid from the headbox 36 on the sphagnum moss slurry in order to form the reinforcing top layer 22. This final layer is identical in terms of consistency and composition to the bottom Kraft wood pulp layer previously deposited except that the flow rate is such as to deposit on a square meter of the wire 20 five grams of solids. The total amount of solids in top, reinforcing Kraft layer 22 and in the bottom reinforcing Kraft layer 24 represents 5.2% by weight of solids in the liquid-absorbent article 14.

The resulting laminated slurry layer Kraft/Sphagnum/ Kraft is then treated with a second re-wetting agent. A re-wetting agent available from Clough Chemicals under the commercial designation G-60 Thorowet, (sodium dioctylsulphosuccinate) has been found satisfactory. Most preferably, the re-wetting agent is delivered on the top Kraft layer in a foamed condition, as described in the Canadian Patent application 2,057,693 in the name of Johnson & Johnson Inc. and laid open on Jun. 14, 1993. The disclosure of this patent application is incorporated herein by reference. The second re-wetting agent is incorporated to laminated slurry in an amount of 0.8% by weight of solids in the absorbent article. In combination, the first and second re-wetting agents should be applied in an amount ranging from about 0.1% to about 3% by weight of solids in the absorbent component, preferably in the range from about 0.1% to about 1.5%.

The slurry layer is then passed over a vacuum slot 50 to extract water under the influence of a pressure differential established across the slurry layer. It is necessary to regulate the residence time of the slurry layer over the vacuum slot 50 and the vacuum intensity in order to control the density of the final product. Generally, decreased vacuum and increased speed will result in a less dense product. Conversely, increased vacuum and decreased speed will produce a denser product.

The web leaving the dewatering station 50 passes through a drier 52 whose purpose is to elevate the temperature of the web to evaporate residual water. The drier 52 is of a well-known construction and does not require a detailed description herein.

It may be envisaged to add between the drier 52 and the vacuum slot 50 a press section (not shown in the drawings) to mechanically express water from the web, as it is well-known to those skilled in the art, in order to reduce the water contents in the web as much as possible before it is processed in the drier 52.

Downstream of the drier 52 a calendering station 54 is provided which mechanically compresses the dried product in order to densify the sphagnum moss material for enhancing its drying power. If desired, the calendering station 54 may be followed by a perf-embossing station (not shown in the drawings) provided to tenderize the web by mechanical working. This treatment softens the sphagnum moss structure for enhancing its comfort potential. The calendering operation is described in detail in the international application PCT/CA92/00308 filed on Jul. 20, 1992 in the name of Johnson & Johnson Inc. The contents of this application is incorporated herein by reference.

An alternative to the perf-embossing technique is the micro-corrugating operation which is similar to the perf-embossing except that no perforations are performed. The liquid-absorbent structure is solely subjected to an embossing operation to create closely spaced hinge lines. The micro-corrugating operation is described in U.S. Pat. Nos. granted to Personal Products Company 4,596,567 and 4,559,050 issued on Jun. 24, 1986 and Dec. 17, 1988 respectively. The contents of these patents is incorporated herein by reference.

Applications of the product and methods of the present invention for sanitary and other health-care uses can be accomplished by any sanitary protection, incontinence, medical and absorbent methods and techniques as are presently or prospectively known to those skilled in the art. Thus, it is intended that the present application covers the modifications and variations of this invention provided that they come within the scope of the appended claims and their equivalents.

We claim:

1. A liquid-absorbent article having a high fluid acceptance rate for use in a disposable liquid-absorbent product, said liquid-absorbent article comprising a mixture of sphagnum moss material having inter-particle interstices and intra-particle interstices and cross-linked fibers, wherein the cross-linked fiber are in an amount effective to increase the inter-particle interstices between the sphagnum moss material and thereby increase fluid acceptance rate of said liquid-absorbent article.

2. A liquid-absorbent article as defined in claim 1, wherein said cross-linked fibers are cellulosic fibers.

3. A liquid-absorbent article as defined in claim 2, wherein said liquid-absorbent article comprises cross-linked cellulosic fibers in the range from about 5% to about 75% by weight of solids in the liquid-absorbent article.

4. A liquid-absorbent article as defined in claim 2, wherein said liquid-absorbent article comprises cross-linked cellulosic fibers in the range from about 15% to about 40% by weight of solids in the liquid-absorbent article.

5. A liquid-absorbent article as defined in claim 2, wherein said liquid-absorbent article comprises cross-linked cellulosic fibers in the range from about 15% to about 30% by weight of solids in the liquid-absorbent article.

6. A liquid-absorbent article as defined in claim 3, wherein said article is in the form of a sheet.

7. A liquid-absorbent article as defined in claim 6, further comprising a fibrous component selected from the group consisting of rayon, polyester, nylon, acrylic, Kraft wood pulp, mechanical wood pulp, cotton linters and mixtures thereof.

8. A liquid-absorbent article as defined in claim 3, wherein said article is mechanically tenderized for increasing softness and flexibility of said article.

9. A liquid-absorbent article as defined in claim 8, wherein said article is mechanically tenderized by a method selected from the group consisting of perf-embossing and micro-corrugating.

10. A liquid-absorbent article as defined in claim 3, comprising a reinforcing layer.

11. A liquid-absorbent article as defined in claim 10, wherein said reinforcing layer provides an outer surface of said article.

12. A liquid-absorbent article as defined in claim 11, wherein said article includes a pair of reinforcing layers in a spaced apart relationship providing two main opposite outer surfaces of said article.

13. A liquid-absorbent article as defined in claim 11, wherein said reinforcing layer includes Kraft wood pulp fibers.

14. A disposable, laminated liquid-absorbent product, comprising:
a) a liquid permeable cover layer;
b) a liquid impervious backing layer; and
c) an absorbent component between said layers, said absorbent component comprising a sheet containing a mixture of sphagnum moss material having inter-particle interstices and intra-particle interstices and cross-linked fibers, wherein the cross-linked fiber are in an amount effective to increase the inter-particle interstices between the sphagnum moss material and thereby increase fluid acceptance rate of said liquid-absorbent article.

15. A disposable, laminated liquid-absorbent product as defined in claim 14, wherein said cross-linked fibers are cellulosic fibers.

* * * * *